United States Patent
Howland

(10) Patent No.: US 6,478,798 B1
(45) Date of Patent: Nov. 12, 2002

(54) SPINAL FIXATION APPARATUS AND METHODS FOR USE

(76) Inventor: Robert S. Howland, 560 Old Ranch Rd., Seal Beach, CA (US) 90740

( * ) Notice: Subject to any disclaimer, the term of this patent is extended or adjusted under 35 U.S.C. 154(b) by 0 days.

(21) Appl. No.: 09/861,278

(22) Filed: May 17, 2001

(51) Int. Cl.[7] .............................................. A61B 17/56
(52) U.S. Cl. ...................................................... 606/61
(58) Field of Search ............................. 606/61, 60, 53, 606/54, 55, 56, 57, 58, 72, 73; 411/392, 383, 389, 378

(56) References Cited

U.S. PATENT DOCUMENTS

| | | | |
|---|---|---|---|
| 4,653,481 A | 3/1987 | Howland et al. | |
| 4,771,767 A | 9/1988 | Steffee | |
| 4,854,311 A | 8/1989 | Steffee | |
| 5,034,011 A | 7/1991 | Howland | |
| 5,084,048 A | * | 1/1992 | Jacob et al. |
| 5,133,716 A | 7/1992 | Plaza | |
| 5,207,678 A | 5/1993 | Harms et al. | |
| 5,226,766 A | 7/1993 | Lasner | |
| 5,261,909 A | * | 11/1993 | Sutterlin et al. |
| 5,380,323 A | * | 1/1995 | Howland |
| 5,487,744 A | * | 1/1996 | Howland |
| 5,496,318 A | 3/1996 | Howland et al. | |
| 5,545,164 A | 8/1996 | Howland | |
| 5,545,166 A | * | 8/1996 | Howland |
| 5,735,850 A | 4/1998 | Baumgartner et al. | |
| 5,782,833 A | 7/1998 | Haider | |
| 5,814,046 A | 9/1998 | Hopf | |
| 5,980,523 A | 11/1999 | Jackson | |
| 6,083,226 A | 7/2000 | Fiz | |

* cited by examiner

Primary Examiner—Pedro Philogene
(74) Attorney, Agent, or Firm—Lyon & Lyon LLP

(57) ABSTRACT

An anchor screw assembly includes a screw having a threaded portion and a head portion to which a swing bolt is pivotally coupled. A clamp assembly includes lower and upper clamp portions that are securable on the swing bolt by a fastener. The clamp portions include noncircular first passages for receiving a noncircular region of the swing bolt therethrough to prevent rotation of the clamp assembly on the swing bolt, and cooperating grooves that together define a second passage. The head portion of the screw includes a shoulder, and the lower clamp portion frictionally engages the shoulder when the clamp assembly is fully secured on the swing bolt, thereby securing the swing bolt relative to the screw. Multiple screw assemblies are screwed into adjacent vertebrae, and a rod is secured within the second passages between the anchor screw assemblies to stabilize the vertebrae.

47 Claims, 8 Drawing Sheets

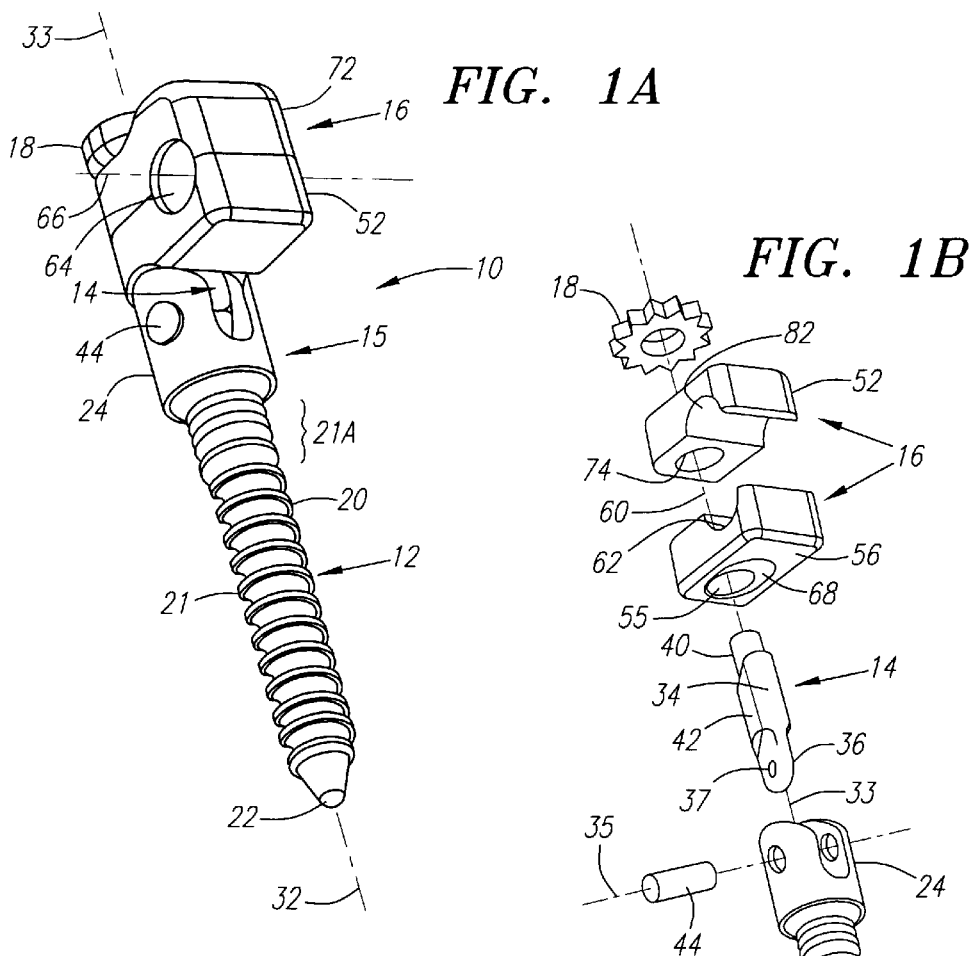
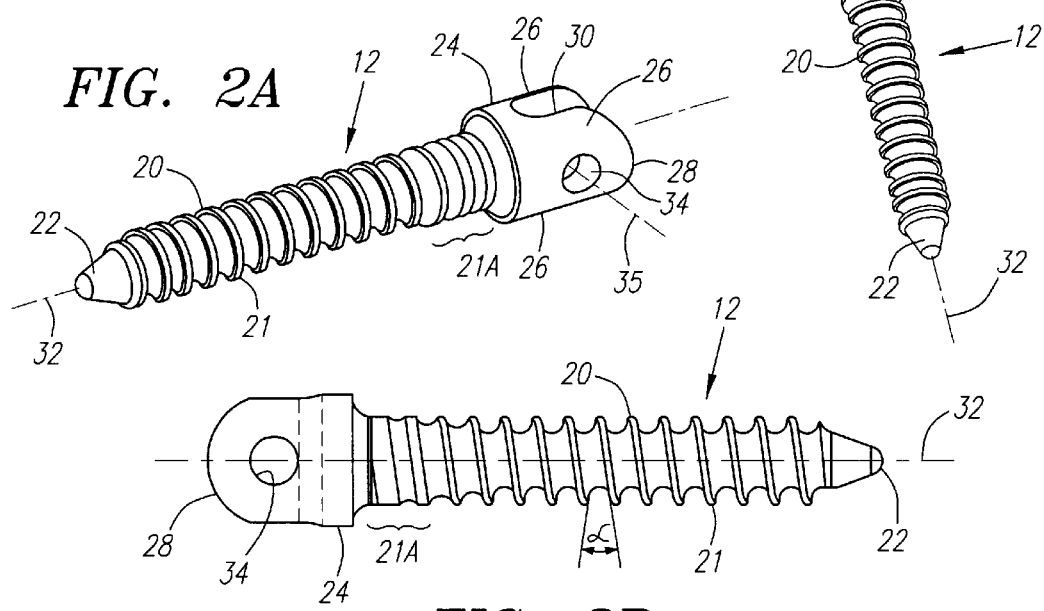

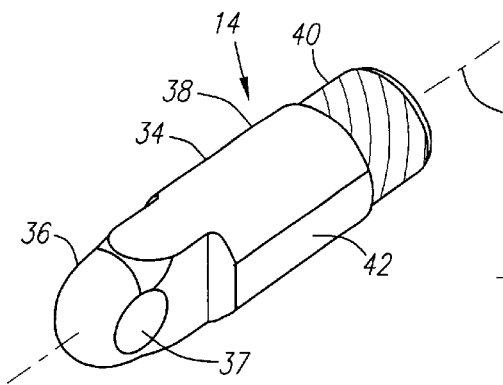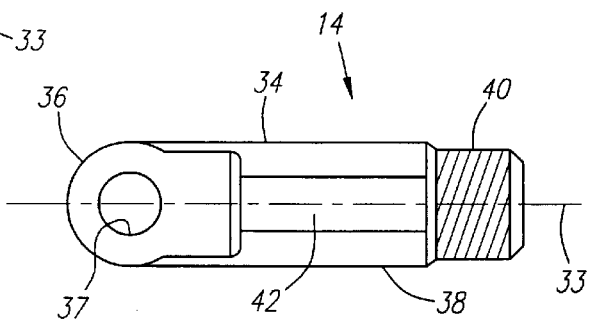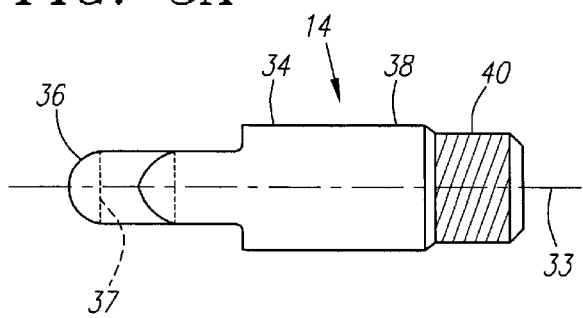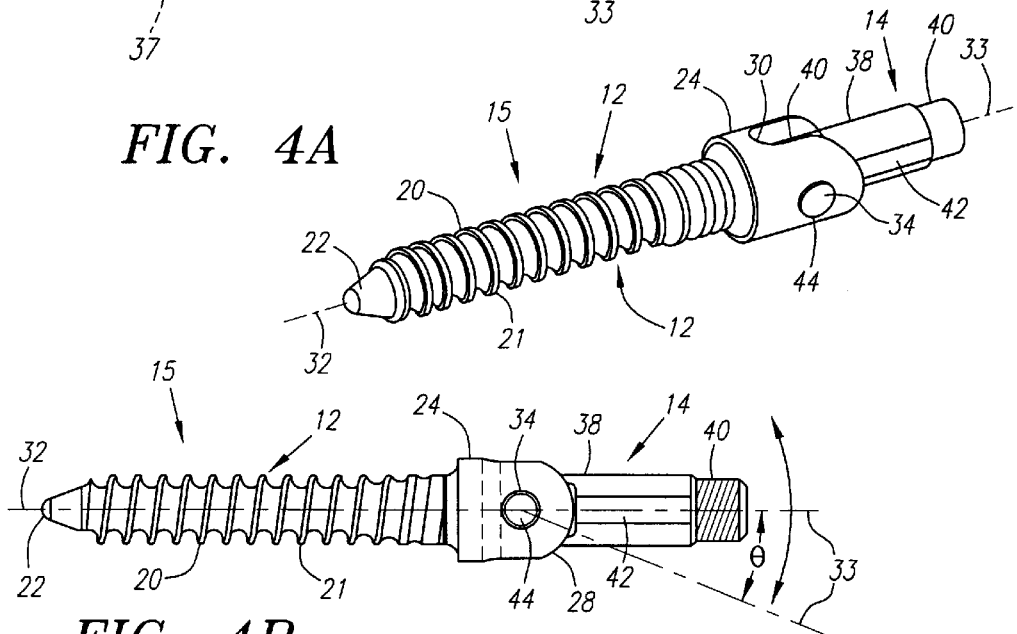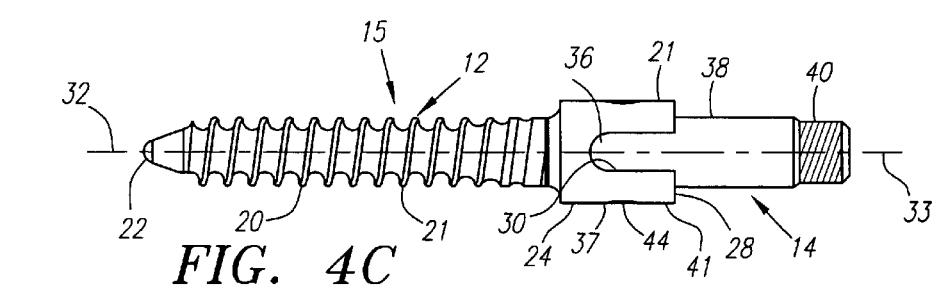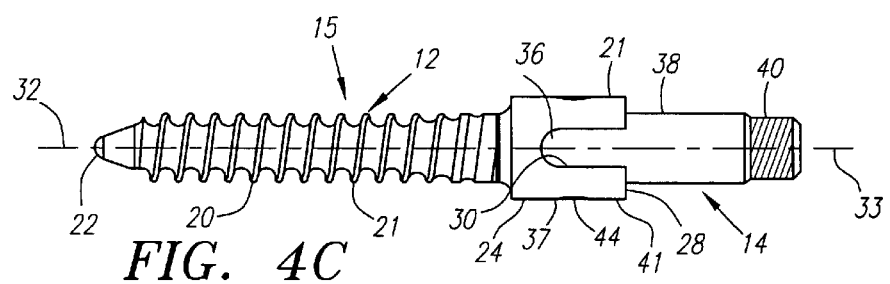

SPINAL FIXATION APPARATUS AND METHODS FOR USE

FIELD OF THE INVENTION

The present invention relates generally to apparatus and methods for treating spinal disorders, and more particularly to anchor screw assemblies, spinal fixation systems including such anchor screw assembles, and methods for stabilizing, adjusting, or otherwise fixing adjacent vertebrae using such spinal fixation systems.

BACKGROUND

Various systems and methods have been suggested for treating spinal disorders, such as degenerative discs, stenosis, trauma, scoliosis, kyphosis, or spondylolisthesis. For example, U.S. Pat. No. 5,545,166, naming the same inventor as the present application, discloses a spinal fixation system that includes a plurality of anchor screws, clamp assemblies, pivot blocks, clamp blocks, and rods that are implanted along a patient's spine to fix two or more adjacent vertebrae relative to one another. The system generally includes a swing bolt anchor screw, a pivot block receivable on the swing bolt, and a clamp block receiving a rod therethrough that is pivotally attachable to the pivot block. In addition, the system includes one. or more fixed anchor screws, and clamp assemblies for receiving the rod therein. The clamp assemblies and pivot block are receivable on the anchor screws by spindles that thread along a threaded portion of the anchor screws.

During use, vertebrae to be treated are surgically exposed, and an arrangement of anchor screws and clamp accessories are selected. For example, a fixed anchor screw may be screwed into each of the vertebrae on either side of a first vertebra. A rod is selected that may extend between the fixed anchor screws and that may be bent to conform to the shape of the anatomy encountered. The rod is inserted through a loose clamp block, and the rod is placed in clamp assemblies that are received over the fixed anchor screws.

A swing bolt anchor screw is then screwed into the first vertebra adjacent the rod, and a pivot block is received on the swing bolt screw. The clamp block and/or pivot block are adjusted such that the clamp block may be engaged with a pivot on the pivot block. A set screw may then be screwed into the clamp block to secure the clamp block to the pivot. A pair of set screws are also screwed into the clamp block to secure the rod within the clamp block. Preferably, a pair of such systems are implanted on either side of the vertebrae.

During the procedure, it may be desirable to adjust the vertebrae relative to one another. Once the system(s) is(are) connected as described above, the set screws may be loosened and the rod(s), clamp block(s), and/or pivot block(s) may be adjusted, e.g., by moving the spindle(s) to adjust the height of the pivot block(s) and/or clamp assemblies on the anchor screws, by pivoting the swing bolt anchor screw(s), and/or pivoting the clamp block(s) relative to the pivot block(s). Once the vertebrae have been moved into a desired position, the set screws may be tightened, and the spindles secured in position by crimping the walls surrounding the spindles.

An advantage of this system is that the swing bolt anchor screw, pivot block, and clamp block arrangement allows adjustment of the system about two axes, i.e., the axis of the swing bolt anchor screw and the axis of the pivot on the pivot block. However, because the system of the '166 patent is polyaxial, i.e., may pivot about multiple axes, there is greater risk of the system coming out of alignment when the patient resumes normal physical activity.

This system is also very complicated, involving six parts, including three set screws, that are mounted on each swing bolt anchor screw. In addition, because the swing bolt is threaded, an intricate spindle device is required in order to allow the pivot block and clamp assemblies to be threaded onto the swing bolt, and still control their orientation about the axis of the swing bolt. Thus, because of its complexity and many intricate parts, this system may be expensive to manufacture and/or difficult to implant.

Accordingly, apparatus and methods for stabilizing, adjusting, and/or fixing vertebrae would be considered useful.

SUMMARY OF THE INVENTION

The present invention is directed to anchor screw assemblies, spinal fixation systems including such anchor screw assembles, and methods for stabilizing, adjusting, or otherwise fixing adjacent vertebrae using such spinal fixation systems.

In accordance with one aspect of the present invention, an anchor screw assembly is provided that includes a screw having a first threaded portion, and a second head portion. A swing bolt is pivotally coupled to the second portion of the screw. The swing bolt defines a first axis, and includes a noncircular region extending along the first axis, the noncircular region having a noncircular cross-section and a substantially smooth wall. In addition, the swing bolt may include a threaded region on its end opposite the screw.

A clamp assembly is provided that includes first and second clamp portions that are receivable on the swing bolt. Each clamp portion has a noncircular first passage therethrough for receiving the noncircular region of the swing bolt therethrough. Thus, the noncircular region and the first passage have like cross-sections, thereby preventing rotation of the clamp assembly with respect to the swing bolt about the first axis when the noncircular region of the swing bolt is received in the first passages.

In addition, the first and second clamp portions have cooperating grooves therein, the cooperating grooves together defining a second passage extending along a second axis substantially transversely to the first axis when the first and second clamp portions are received on the swing bolt. The clamp assembly also defines a third axis extending along a centerline of the clamp assembly, e.g., from the first passage towards the second passage. The second axis, and consequently the second passage, may extend substantially perpendicular to the third axis, or may define an acute angle with the third axis.

A fastener is also provided for securing the clamp assembly on the swing bolt. Preferably, the fastener is a nut, such as a twelve (12) point nut or a hex nut, that may be threaded onto the threaded region of the swing bolt to secure the clamp assembly on the swing bolt.

In a preferred embodiment, the second portion of the screw includes a shoulder, and the clamp assembly may substantially engage the shoulder when the clamp assembly is fully secured on the swing bolt, thereby preventing the swing bolt from pivoting with respect to the screw. More preferably, the shoulder is radiused about a pivot point on the second portion, and the lower clamp portion includes a recess adjacent its lower surface that intersects the first passage. The recess has a matching radiused shape for slidably receiving the shoulder therein as the clamp assembly pivots about the pivot point, i.e., before the clamp assembly is fully secured on the swing bolt.

In accordance with another aspect of the present invention, a spinal fixation system is provided that includes a first anchor screw assembly, such as that described above. The first anchor screw assembly includes a first screw having a threaded portion, and a swing bolt pivotally coupled to the screw and including a noncircular region. The spinal fixation system also includes a plurality of clamp assemblies, including a first passage for receiving the first swing bolt therethrough, and a second passage for receiving an elongate member, e.g., a substantially rigid rod, therethrough. The dimensions of each clamp assembly may be different, e.g., including a second passage that is at one of a plurality of distances from the first passage and/or that is oriented at a predetermined angle along the clamp assembly.

For example, a first clamp assembly may include a first passage for receiving the first swing bolt therethrough. The first passage has a similar cross-section to the noncircular region of the swing bolt. The first clamp assembly includes a second passage therethrough along a second axis substantially transverse to the first axis. A fastener may be used for securing the first clamp assembly on the swing bolt. Thus, when the first clamp assembly is received on the first swing bolt, the first clamp assembly is fixed in a predetermined orientation with respect to a first pivot axis of the first swing bolt.

The spinal fixation system also includes a second anchor screw assembly including a second screw having a threaded portion and a hub, and a second clamp assembly receivable on the hub. The second screw may be a fixed screw or, preferably, a swing bolt anchor screw, similar to that described above. The second clamp assembly includes a third passage therethrough along a third axis. The second screw assembly may be oriented, when implanted, such that the third axis is substantially transverse to the first axis. Optionally, additional anchor screw assemblies may also be provided.

Finally, the spinal fixation system also include an elongate member, such as a substantially rigid rod, that is receivable through the second and third passages.

In accordance with another aspect of the present invention, a method is provided for simple alignment or otherwise stabilizing vertebrae relative to one another using a plurality of swing bolt anchor screw assemblies, such as those described above. A threaded portion of a first swing bolt anchor screw is screwed into a first vertebra until a first pivot axis of the first swing bolt anchor screw is generally parallel to the spinal axis. A threaded portion of a second swing bolt anchor screw is screwed into a second vertebra adjacent the first vertebra until a second pivot axis of the second swing bolt anchor screw is substantially transverse to the first pivot axis. If desired, a third anchor screw (or more) may be screwed into other vertebra adjacent to the first vertebra.

An angle of one or more swing bolts on the first and second swing bolt anchor screws may be adjusted about the first and second pivot axes. Lower clamp portions may be placed on the swing bolts of the first and second swing bolt anchor screws, either before or after the angle adjustments described above. A rod may be placed on the lower clamp portions, e.g., when the grooves in the lower clamp portions have been properly aligned with one another. Thus, the rod may extend between the first and second anchor screws, and between any additional anchor screws added generally in a straight line. In addition, if desired, the rod may be bent, e.g., in a single plane, to a predetermined configuration based upon anatomy encountered before securing the rod on the swing bolts. Preferably, the rod is bent and secured to the clamp assemblies such that it is curved in the sagetal plane (the plane that may be seen from a lateral view of the patient) and substantially straight in the coronal plane (the plane that may be seen from an anterior or posterior view of the patient).

Upper clamp portions may be secured on the swing bolts of the first and second swing bolt anchor screws, thereby securing the rod between the upper and lower clamp portions. For example, a nut or other fastener may be threaded onto the swing bolt after the upper and lower clamp portions, thereby securing the rod between the upper and lower clamp portions and/or securing the clamp assemblies on the swing bolts. These fasteners may also be loosened to allow adjustment of the vertebrae relative to one another, and then the fasteners may again be tightened to fix the vertebrae in desired relative positions.

Other objects and features of the present invention will become apparent from consideration of the following description taken in conjunction with the accompanying drawings.

BRIEF DESCRIPTION OF THE DRAWINGS

FIG. 1A is a perspective view of a preferred embodiment of an anchor screw assembly, in accordance with the present invention.

FIG. 1B is an exploded perspective view of the anchor screw assembly of FIG. 1A.

FIGS. 2A and 2B are perspective and side views, respectively, of a screw for the anchor screw assembly of FIGS. 1A and 1B.

FIGS. 3A–3C are perspective and first and second side views, respectively, of a swing bolt for the anchor screw assembly of FIGS. 1A and 1B.

FIGS. 4A–4C are perspective and first and second side views, respectively, of an assembled screw and swing bolt for the anchor screw assembly of FIGS. 1A and 1B.

FIGS. 5A–5C are perspective and first and second side views, respectively, of a first embodiment of a lower clamp portion for a clamp assembly, in accordance with the present invention.

FIGS. 6A–16C are perspective and first and second side views, respectively, of a first embodiment of an upper clamp portion for a clamp assembly, in accordance with the present invention.

FIGS. 8–8E are perspective views of alternative embodiments of an upper clamp portion, in accordance with the present invention.

FIG. 11 shows a pair of spinal fixation systems implanted along a patient's spine.

DETAILED DESCRIPTION OF THE PREFERRED EMBODIMENTS

Figures 5A, 5B, 5C, 6A, 6B, 6C:
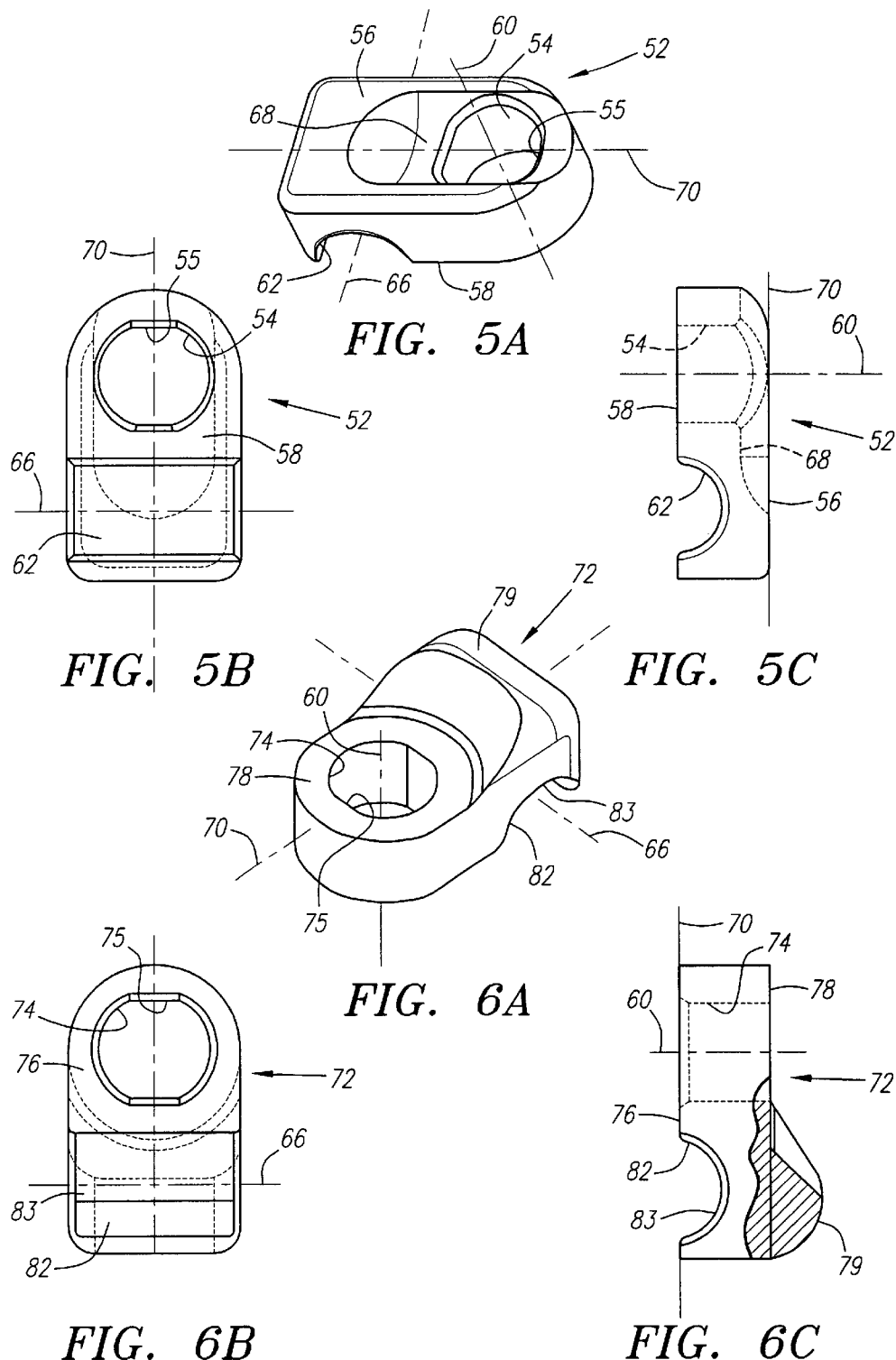

Turning now to the drawings, FIGS. 1–6 show a first preferred embodiment of an anchor screw assembly 10, in accordance with the present invention. Generally, the anchor screw assembly 10 includes a screw 12, a swing bolt 14 pivotally coupled to the screw 12 to provide an anchor screw 15, and a clamp assembly 16 securably received on the swing bolt 14, as shown in FIGS. 1A and 1B. All of the components of the anchor screw assembly 10 may be made from a variety of biocompatible materials, e.g., metals, and preferably from titanium or alloys including titanium.

With particular reference to FIGS. 2A and 2B, the screw 12 generally includes a first threaded portion 20 terminating in a tip 22, and a second head portion 24 opposite the tip 22. The threaded portion 20 may include a helical thread 21 defining a thread pattern, preferably configured for substantially securing the screw 12 into bone, such as a portion of a vertebra (not shown). The thread spacing may be between about three to six threads per centimeter (3–6 threads/cm), and preferably about 4.8 threads per centimeter (about 12 threads per inch). The thread spacing may be substantially constant between the tip 22 and the head portion 24 or may vary along the length of the threaded portion 20.

The leading and trailing edges of axially adjacent portions of the thread 21 may define an inclusive angle "alpha" between them of between about twenty to forty degrees (20–40°), and preferably about thirty degrees (30°). Preferably, each thread 21 tapers outwardly from the root diameter to the major diameter of the thread 21, such that the leading and trailing edges on either side of a portion of the thread 21 define tangent lines that intersect one another adjacent the outer edge of the respective portion of the thread 21. The thread 21 may have a height of between about 0.50–3.00 millimeters, and preferably between about 0.60–2.00 millimeters.

The threaded portion 20 may have desired dimensions to accommodate threading into bone, such as a vertebra (not shown). For example, the threaded portion 20 may have an outer diameter between about 3.5–8.5 millimeters, preferably between about 5.8–8.5 millimeters, and a length between about 25–65 millimeters, and preferably between about 35–65 millimeters. The threaded portion 20 may have a substantially uniform major and minor diameter along its length. Alternatively, the threaded portion 20 may have a taper, e.g., reducing in minor and/or major diameter from the head portion 24 towards the tip 22. The thread 21 may have a substantially uniform height, or may become increasingly higher from the head portion 24 towards the tip 22, e.g., if the threaded portion 20 is tapered, to provide a substantially uniform outer diameter for the threaded portion 20.

Preferably, the threaded portion 20 includes a pull-out portion 21A. For example, the final two threads 21A before the head portion 24 may include a minor diameter that gradually expands out to the major diameter. In addition or alternatively, the final two threads 21A may have a plateau on their outer edge. This pull-out portion 21A may facilitate manufacturing of the anchor screw 12 and/or may improve engagement of the screw 12 with bone into which the screw 12 is threaded. Other thread patterns and screw designs that may be appropriate for use in an anchor screw assembly in accordance with the present invention may be found in U.S. Pat. Nos. 4,854,311, 5,034,011, and 5,226,766, the disclosures of which are expressly incorporated herein by reference.

The head portion 24 generally has a cross-section larger than the threaded portion 20 and includes a full-radius shoulder 28 opposite the threaded portion 20. The shoulder 28 includes a predetermined radius about a pivot axis 35 to facilitate pivoting of the swing bolt 14 and/or the clamp assembly 16 (not shown in FIGS. 2A and 2B) with respect to the head portion 24, as explained further below. The head portion 24 includes a slot 30 therein extending generally parallel to a longitudinal axis 32 of the screw 12, thereby dividing the head portion 24 into ears 26. Pin holes 34 extend through the ears 26 along the pivot axis 35, i.e., substantially perpendicular to the longitudinal axis 32.

Turning to FIGS. 3A–3C, the swing bolt 14 includes an elongate body 34 including a first looped region 36, a second noncircular intermediate region 38, and a third threaded region 40 generally opposite the looped region 36. The looped region 36 may be substantially narrower than the other regions of the swing bolt 14, i.e., having a width slightly smaller than a width of the slot 30 in the screw 12 such that the looped region 36 may be received in the slot 30 between the ears 26, as shown in FIGS. 4A–4C. The looped region 36 has a pin hole 37 therethrough that extends substantially perpendicular to the longitudinal axis 32.

The noncircular region 38 of the swing bolt 14 is preferably substantially smooth-walled and has a noncircular cross-section, preferably for slidably receiving the clamp assembly 16 thereon (see FIGS. 1A and 1B), while preventing rotation of the clamp assembly 16 about longitudinal axis 33. In the preferred embodiment shown in FIGS. 3A–3C, one or more flat walls 42, and preferably two opposing flat walls, are formed along the intermediate region 38. Thus, the cross-section may define a parallel side shape, a "D" shape, or, alternatively, a hexagon, a square, a star, or other geometric shape.

As shown in FIGS. 4A–4C, the looped region 36 of the swing bolt 14 may be received in the slot 30 of the head portion 24, and a pin 44 may be received through the pin holes 34, 37 to provide anchor screw 15. The pin 44. may fix the swing bolt 14 to the screw 12, while allowing the swing bolt 14 and screw 12 to pivot with respect to one another such that the longitudinal axes 32, 33 intersect, but define an angle "theta" greater than zero degrees, as shown in phantom in FIG. 4B.

Turning to FIGS. 5A–6C, the clamp assembly 16 (shown in FIGS. 1A and 1B) generally includes a first lower clamp portion 52 and a second upper clamp portion 72. The lower and upper clamp portions 52, 72 have noncircular bolt passages 54, 74 that extend entirely through them between lower surfaces 56, 76 and upper surfaces 58, 78, respectively, thereby defining a first axis 60. The bolt passages 54, 74 preferably have a cross-section similar to the cross-section of the noncircular region 42 of the swing bolt 14 (see FIGS. 1B, 3A, 3B, 4A, and 4B). Thus, the bolt passages 54, 74 may accommodate receiving the swing bolt 14 therethrough, while preventing rotation of the clamp assembly 16 on the swing bolt 14, as explained further below.

In addition, the lower and upper clamp portions 52, 72 have generally semi-cylindrical grooves 62, 82 therein that cooperate with one another when the clamp assembly 16 is assembled to define a rod passage 64, as shown in FIG. 1A. The rod passage 64 generally extends along a second axis 66 that is substantially transverse to, and preferably substantially perpendicular to, the first axis 60. In the embodiment shown, the second axis 66 is also substantially perpendicular to a third axis 70 that extends along a length of the lower clamp portion 52 substantially perpendicular to both the first and second axes 60, 66 (thus, the three axes 60, 66, 70 may be orthogonal to one another). The rod passage 64 has a cross-section similar to a rod (not shown) that may be received therein. For example, the cross-section may be generally circular, but preferably is noncircular, e.g., circular with one or more flattened walls, such as wall 83 shown in the upper clamp portion 72 in FIGS. 6B and 6C. Alternatively, the rod passage 64 may have other geometric shapes, similar to the bolt passages 54, 74, described above. In a further alternative, one or both of the grooves 62, 82 may include teeth or other serrations (not shown) for enhancing engagement with a rod received in the rod passage 64, either alone or in combination with one of the cross-sections described above. Exemplary serrations are shown in U.S. Pat. No. 5,545,164, the disclosure of which is expressly incorporated herein by reference.

With particular reference to FIGS. 6A–6C, the groove 82 in the upper clamp portion 72 extends along the lower surface 76. The upper surface 78 may be recessed above the bolt passage 174, thereby accommodating a fastener (not shown) thereon, while minimizing the profile of the resulting clamp assembly. For example, the groove 82 may define a shoulder 79 that may be higher than the upper surface 78. The shoulder 79 may have a height similar to a nut or other fastener (not shown) that may be attached to a swing bolt (also not shown) that is inserted through the bolt passage 74. Thus, when the fastener engages the upper surface 78, the upper surface of the fastener may define a height similar to the shoulder 79, thereby substantially minimizing a profile of the anchor screw assembly and/or reducing tissue irritation.

With particular reference to FIGS. 5A–5C, the groove 62 in the lower clamp portion 52 extends along the upper surface 58. In addition, the lower clamp portion 62 also includes a recess 68 in the lower surface 56 that intersects the bolt passage 54. The recess 68 preferably has a radius of curvature similar to the shoulder 28 on the head portion 24 of the screw 12 (see FIGS. 4A–4C), as explained further below.

Returning to FIGS. 1A and 1B, the lower surface 76 of the upper clamp portion 72 and the upper surface 58 of the lower clamp portion 52 are substantially flat such that the lower and upper clamp portions 52, 72 may substantially abut one another to provide the rod passage 64. Alternatively, the upper and lower surfaces 58, 76 may include mating segments, e.g., cooperating tabs and slots or other male/female connectors (not shown), that may positively engage one another when the lower and upper clamp portions 52, 72 are disposed in the proper orientation.

The clamp assembly 16 may be received on the swing bolt 14, e.g., by orienting the clamp assembly 16 such that the bolt passages 54, 74 are properly aligned with the noncircular region of the swing bolt. The lower clamp portion 52 may be directed over the swing bolt 14 and then the upper clamp portion 72 may be received over the swing bolt 14, i.e., through the bolt passages 54, 74, respectively. A fastener, e.g., nut 18, may be threaded onto the threaded region 40 of the swing bolt 14 until it engages upper surface 78 of the upper clamp portion 72, thereby forcing the clamp assembly 16 towards the head portion 24 of the screw 12. Consequently, the lower clamp portion 52 may abut the head portion 24 such that the shoulder 28 is received in the recess 68 in the lower surface 56.

Preferably, because of the mating shapes of the shoulder 28 and recess 68, the lower clamp portion 52 may slide along the shoulder 28 as the swing bolt 14 is pivoted with respect to the screw 12. Once a desired angle is obtained, the nut 18 may be further tightened until the wall of the recess 68 frictionally engages the shoulder 28, thereby substantially securing the swing bolt 14 at the desired angle relative to the screw 12.

Figure 7A:
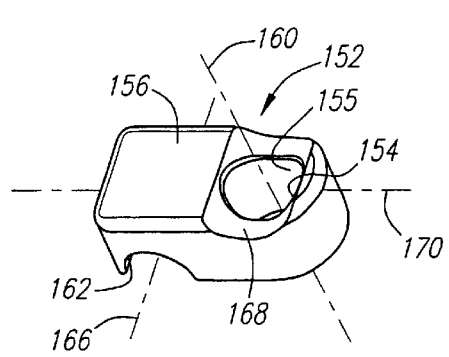
FIGS. 7A–7E are perspective views of alternative embodiments of a lower clamp portion, in accordance with the present invention.

Turning to FIGS. 7A–8E, several alternative embodiments of lower and upper clamp portions are shown that together may provide clamp assemblies that may be received over the screw assembly 15 of FIGS. 4A–4C. For example, the lower and upper clamp portions 152, 172 shown in FIGS. 7A and 8A are generally similar to that shown in FIGS. 5A and 6A, except that the flat regions 155, 175 of the bolt passages 154, 174 are offset ninety degrees from the previous embodiment. The resulting clamp assembly (not shown) may be mounted similar to the previous embodiment, but offset ninety degrees with respect to the anchor screw (not shown).

Figure 7B:
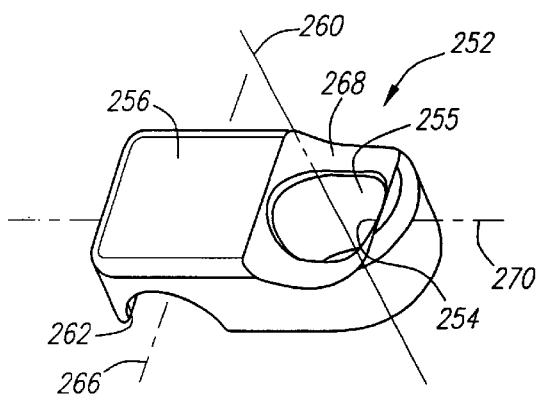
Figure 8A:
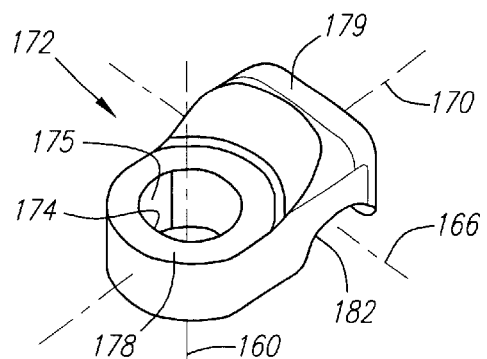
Figure 8B:
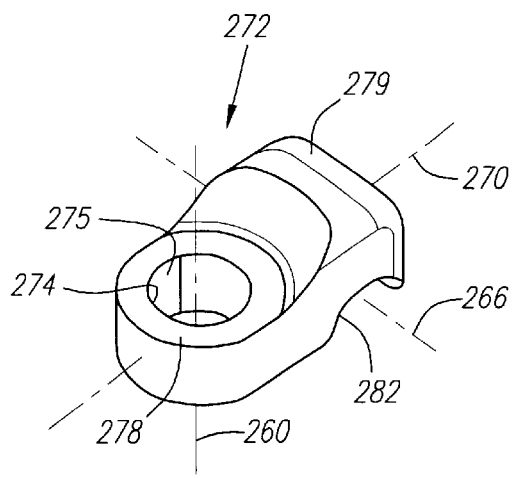

Turning to FIGS. 7B and 8B, another set of lower and upper clamp portions 252, 272 are shown that are similar to the embodiments of FIGS. 7A and 8A, except that the grooves 262, 282 are located further away from the bolt passages 254, 274 along the third axis 270. The resulting clamp assembly from these embodiments may be mounted on the anchor screw similar to the previous embodiment. A rod received in the resulting rod passage, however, will be disposed further from the anchor screw than the previous embodiment.

Figure 7C:
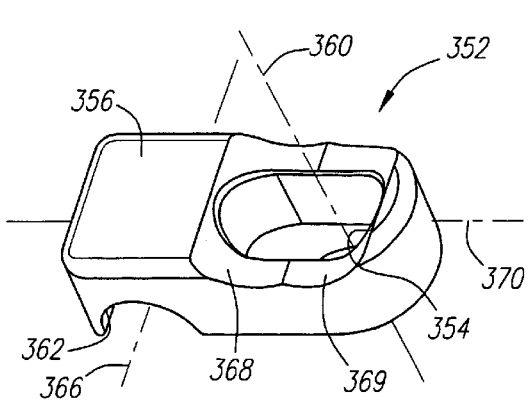
Figure 8C:
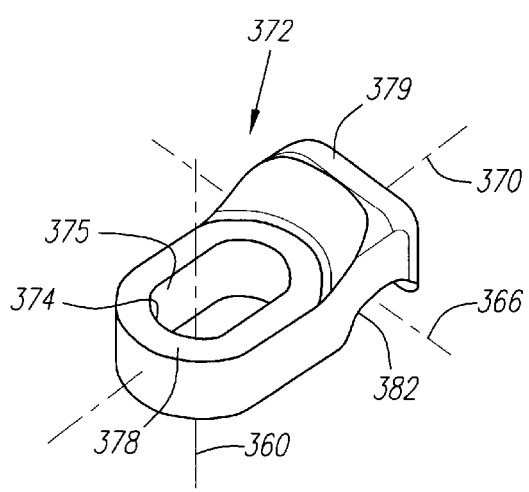

Turning to FIGS. 7C and 8C, yet another set of lower and upper clamp portions 352, 372 are shown that are similar to the embodiments of FIGS. 7A and 8A, except that the bolt passages 354, 374 have an elongated elliptical shape extending along the third axis 370. In addition, the lower surface 356 of the lower clamp portion 352 includes adjacent recesses 368, 369 that intersect the bolt passage 354 and may overlap one another. The resulting clamp assembly from this embodiment may be secured to the anchor screw such that either of the recesses 368, 369 slidably engages the shoulder of the screw (not shown), thereby allowing a rod (also not shown) received in the rod passage to be disposed at two possible locations, e.g., distances, relative to the anchor screw. optionally, more than two recesses (not shown) may be provided, thereby allowing the rod passage to be disposed at multiple distances from the anchor screw.

Figure 7D:
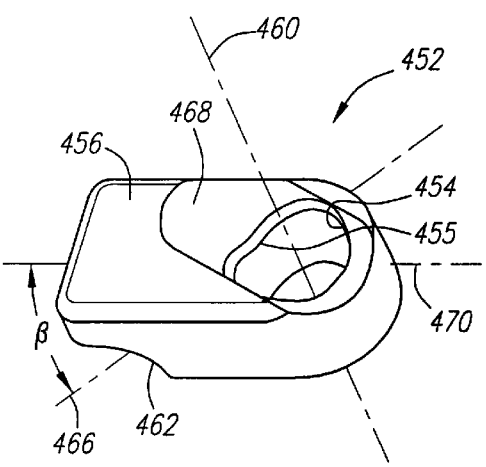
Figure 8D:
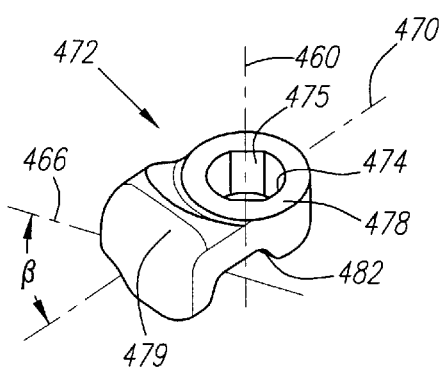

Turning to FIGS. 7D and 8D, still another set of lower and upper clamp portions 452, 472 are shown that are similar to the embodiments of FIGS. 5A and 6A, except that the grooves 462, 482 are aligned such that the second axis 466 defines an angle "beta" with the third axis 470. Preferably, the angle "beta" is between about ten and seventy degrees (10–75°), and more preferably between about forty five and sixty degrees (45–60°). In addition, the flattened wall regions 455, 475 are aligned substantially parallel to the second axis 466, thereby also defining an angle "beta" with respect to the third axis 470.

Figure 7E:
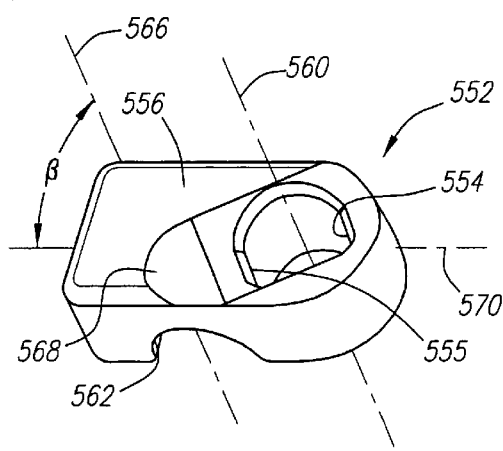
Figure 8E:
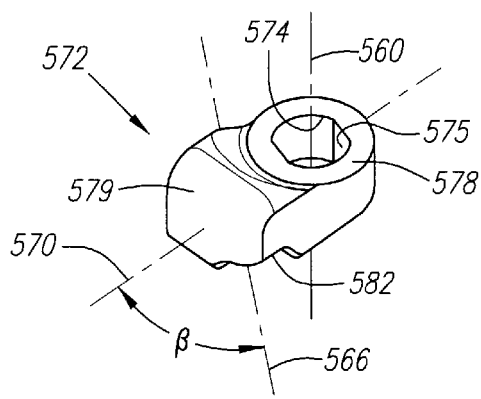

Turning to FIGS. 7E and 8E, another set of lower and upper clamp portions 552, 572 are shown that are similar to the embodiments of FIGS. 7D and 8D, except that the bolt passages 554, 574 and grooves 562, 582 are mirror opposites or opposite-hand of those in the previous embodiment. Thus, it will be appreciated by those skilled in the art that a variety of clamp assemblies may be providing including a range of dimensions, e.g., lengths, thicknesses, "beta" angles, and the like.

Figure 9A:
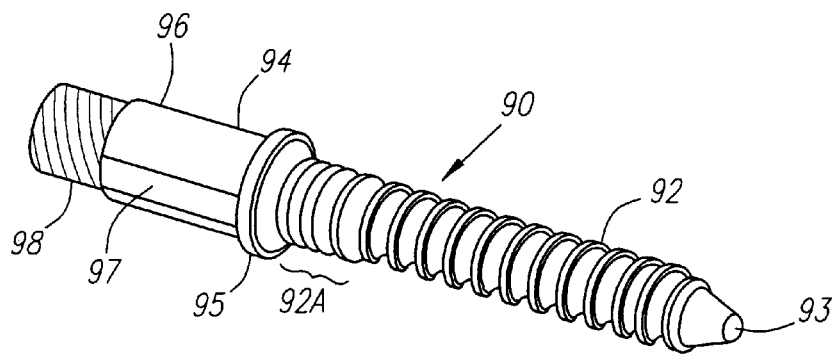
FIGS. 9A and 9B are perspective and side views, respectively, of another embodiment of an anchor screw, in accordance with the present invention.
Figure 9B:
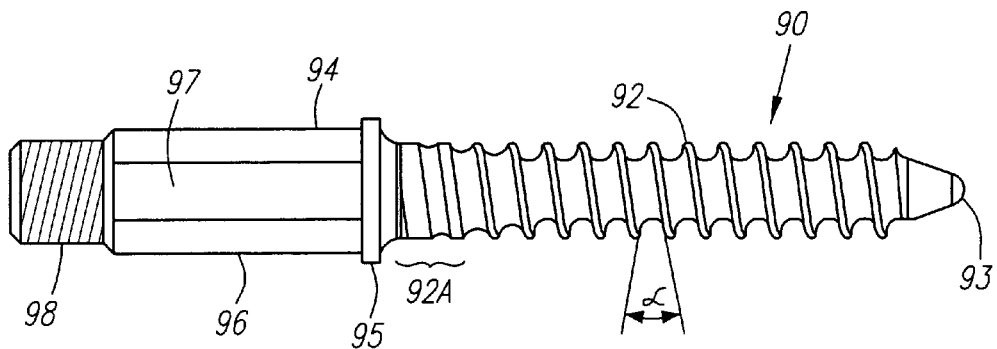

Turning to FIGS. 9A and 9B, another preferred embodiment of an anchor screw 90 is shown that includes a threaded portion 92 terminating in a tip 93, and an enlarged head portion 94 including a noncircular region 96 and a threaded region 98 opposite the tip 93. The threaded portion 92 may include any of the dimensions described above for the anchor screw 12 of FIGS. 2A–2C, e.g., thread pattern, outer diameter, taper, and the like. Preferably, the threaded portion 92 includes a pull-out portion 92A, similar to the swing bolt anchor screw 12. The noncircular region 96 has a cross-section similar to the previously described embodiments, e.g., a generally circular cross-section with one or more flattened wall regions 97. A raised ledge 95 may be provided between the noncircular region 96 and the threaded portion 92.

The threaded region 98 may receive a fastener, such as the nut described above (not shown), e.g., to substantially secure a clamp assembly (also not shown) on the noncircular region 96, similar to the embodiment described above. Thus, the anchor screw 90 may receive any of the clamp assemblies described above.

To provide a system for treating vertebrae of a patient, a set of anchor screws, e.g. pivoting and/or fixed, clamp assemblies, and fasteners may be selected based upon the specific vertebrae being treated and/or based upon the anatomy encountered. A system in accordance with the present invention provides a modularity that may easily accommodate a variety of anatomy and patients.

Turning to FIGS. 10A–10C and 11, an exemplary system 1000 is shown that includes a pair of rods 1002 that are each implanted along a spinal column using three swing bolt anchor screws 1010–1014 and three clamp assemblies, 1016–1020. Alternatively, one or more of the swing bolt anchor screws, such as the outside anchor screws 1010, 1014, may be replaced with nonpivoting anchor screws (such as that shown in FIGS. 9A and 9B). In a further alternative, fewer or additional anchor screws may be implanted, e.g., to secure a shorter or longer rod and/or to fix fewer or additional vertebrae.

Figure 11:
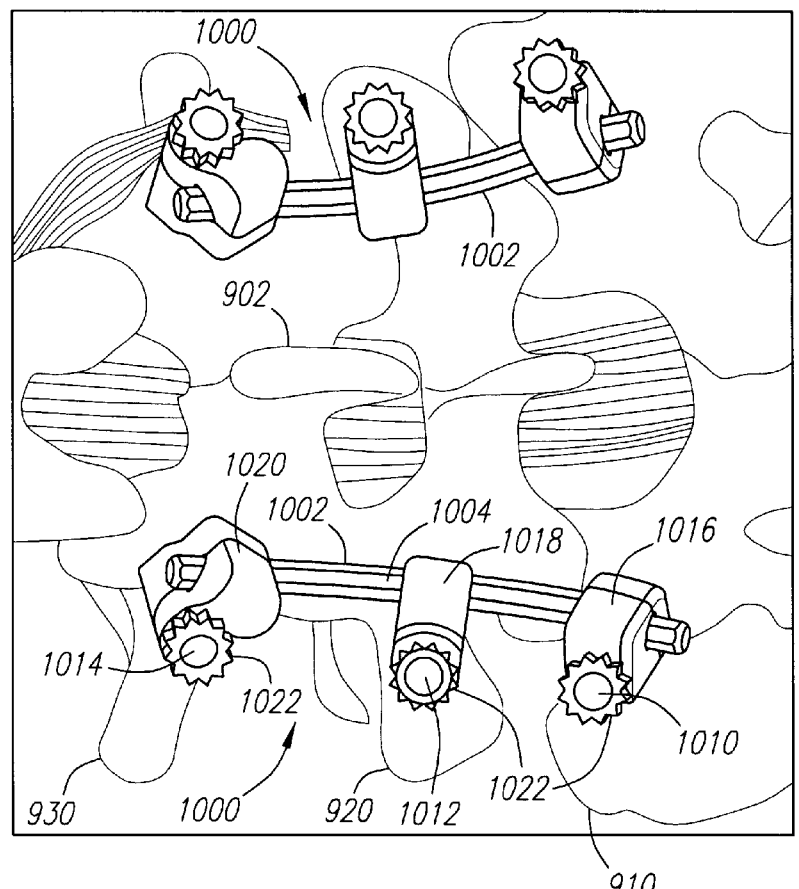

Preferably, the rods 1002 are implanted generally parallel to the central spinal axis on either side of the spinous processes 902, as shown in FIG. 11. The system 1000 may be used to provide adjustment of the vertebrae, e.g., to allow vertical or horizontal, medial or lateral adjustment. Although an implantation procedure for only one rod 1002 is described below, it will be appreciated that a second rod (or even additional rods) may be implanted using a similar procedure.

Figure 10A:
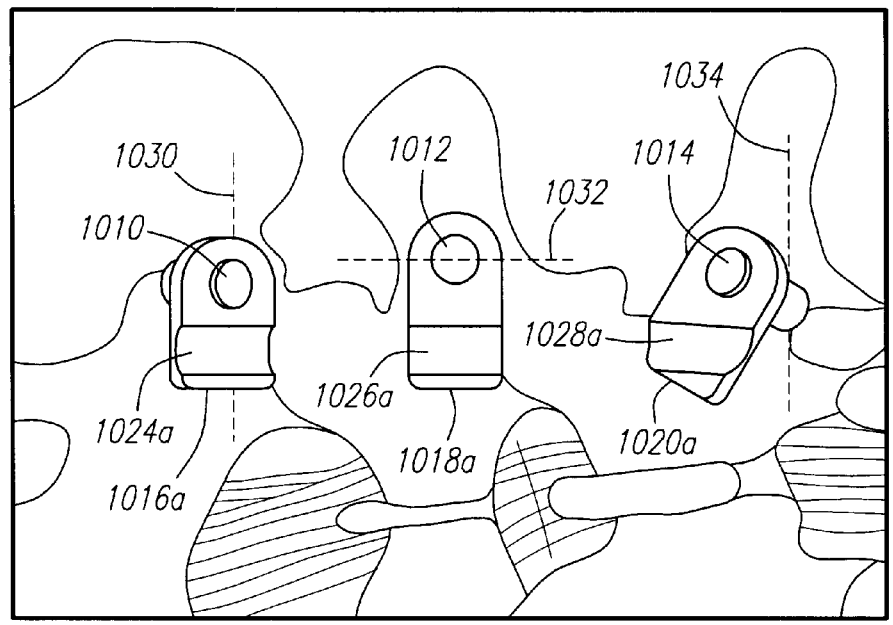
FIGS. 10A–10C show a spinal fixation system being implanted between vertebrae of a patient, in accordance with the present invention.

Turning first to FIG. 10A, the vertebrae, e.g., vertebrae 910, 920, 930, to be stabilized are exposed, e.g., using conventional surgical procedures. The anchor screws 1010–1014 are screwed into the vertebrae 910–930, respectively, e.g., into the pedicles, generally in a substantially straight line. Preferably, the anchor screws 1012–1014 are screwed in sufficiently to provide a predetermined pivot axis with respect to a centerline spinal axis of the patient. For example, the anchor screw 1012 may be screwed until a pivot axis 1032 of the anchor screw 1012 is disposed generally parallel to the centerline spinal axis. In contrast, the other anchor screws 1010, 1014 may be screwed into their respective vertebra until their respective pivot axes 1030, 1034 are disposed substantially transverse to the first pivot axis 1032, and preferably substantially perpendicular to the centerline spinal axis.

Clamp assemblies 1016–1020 are selected based upon the anatomy encountered. For example, the clamp assembly 1016 may be similar to the clamp assembly 152, 172 shown in FIGS. 7A and 8A, and the clamp assembly 1018 may be similar to the clamp assembly 252, 272 of FIGS. 7B and 8B, i.e., having a longer length than the clamp assembly 1016. Finally, the clamp assembly 1020 may be similar to the clamp assembly 552, 572 shown in FIGS. 7E and 8E, i.e., having a groove 1028a (see FIG. 10A) that extends acutely with respect to a centerline length of the clamp assembly 1020.

Figure 10B:
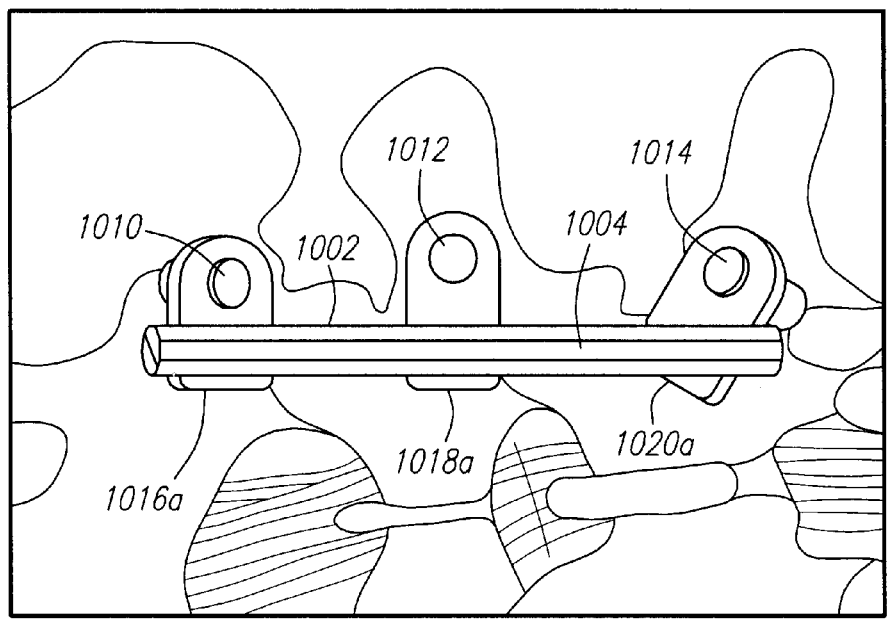

The lower clamp portions of the clamp assemblies 1016a–1020a may be received over the noncircular regions (not shown) of the anchor screws 1010–1014, as best seen in FIG. 10A. A rod 1002 may be received in the grooves 1024a–1028a in the lower clamp portions 1016a–1020a, thereby extending between the anchor screws 1010–1014, as shown in FIG. 10B. If desired, the rod 1002 may be bent to a predetermined shape, as needed, to conform to the anatomy encountered. Preferably, the rod 1002 is bent in only one plane, e.g., the sagetal plane, while remaining substantially straight in the coronal plane. "Sagetal" plane, as used herein, refers to the plane that may be seen from a lateral view of the patient, e.g., that is disposed vertically when the patient is lying face-down. "Coronal" plane refers to the plane that may be seen from an anterior or posterior view of the patient, e.g., that is disposed substantially horizontally when the patient is lying face-down.

In addition, if the rod 1002 includes one or more flattened regions 1004, the flattened region(s) 1004 may be oriented so that they may engage similar flattened regions (not shown) in the rod passages 1024–1028 in the clamp assemblies 1016–1020 (e.g., in the upper clamp portions 1016b–1020b).

One or more of the clamp assemblies 1016–1020 may be adjusted at any time during the procedure. By adjusting the clamp assemblies 1016–1020, the swing bolts on the anchor screws 1010–1014 may be pivoted about their respective pivot axes 1030-1034 with respect to the threaded portions that have been threaded into the vertebrae 910–930. For example, the lower clamp portions 1016a–1020a may be adjusted before and/or after the rod 100 is received in the grooves 1024a–1028a. Because the pivot axes 1030–1034 of the swing bolt anchor screws 1010–1014 are substantially transverse with respect to one another, a uniaxial device (i.e., pivoting in a single axis) may be used to provide multiple degrees of freedom for moving the clamp assemblies 1016–1020 relative to the rod 1002. This may minimize the amount of bending required of the rod 1002, preferably requiring bending in only one plane (preferably, the sagetal plane), thereby substantially maximizing the rigidity of the rod 1002.

Figure 10C:
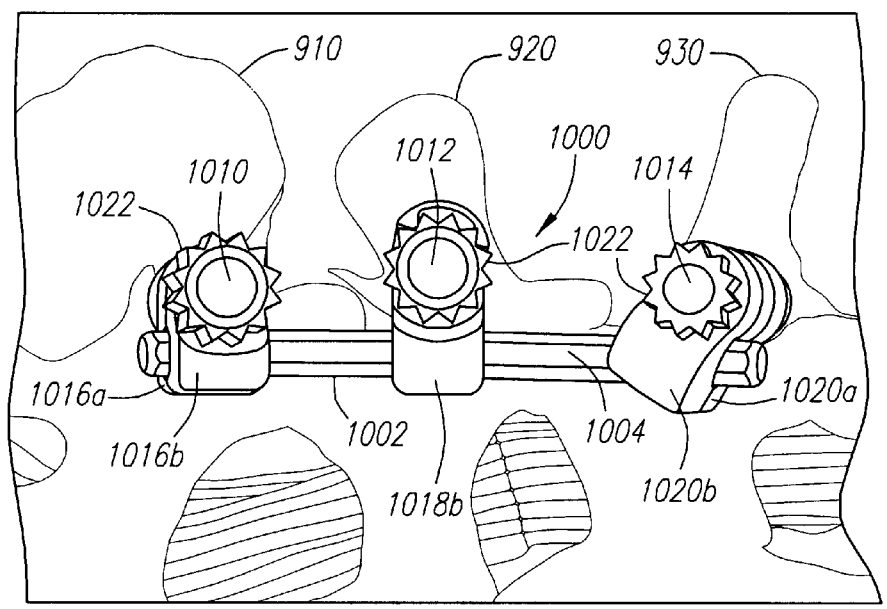

As shown in FIG. 10C, upper clamp portions 1016b–1020b may be placed on the lower clamp portions 1016a–1020a, i.e., received on the swing bolts of the anchor screws 1010–1014. When properly placed, the grooves (not shown) in the upper clamp portions 1016b–1020b substantially engage the rod 1002. Fasteners, such as nuts 1022, may then by threaded onto the swing bolts, thereby substantially securing the rod 1002 between the upper and lower clamp portions 1016–1020.

Preferably, the nuts 1022 are twelve point jam nuts. The nuts 1022 may have rounded upper edges, which may minimize tissue irritation, e.g., of tissue overlying the nuts 1022 after implantation of the system 1000. In addition, the nuts 1022 may include a crimpable rim (not shown), which may be crimped when the nuts are tightened to a desired torque, e.g., to prevent subsequent loosening of the nuts. Alternatively, hex nuts or other fasteners may be used.

Preferably, the lower clamp portions 1016a–1020a include recesses (not shown) that intersect bolt passages through them and the threaded portion of the anchor screws 1010–1014 include radiused shoulders (not shown), as described above. Thus, as the angles of the swing bolts are adjusted, the shoulders may pivotally slide along the surfaces of the recesses of the lower clamp portions 1016a–1020a. Once a desired configuration is obtained, the nuts 1022 may be tightened, thereby causing the lower clamp portions 1016a–1020a to frictionally engage the shoulders and secure the swing bolts with respect to the threaded portions without substantially moving one or more of the vertebrae out of the desired position.

If it desired to adjust the vertebrae 910–930 with respect to one another, the nuts 1022 may be loosened, and the vertebrae 910–930 adjusted, thereby possibly changing the angle of one or more of the clamp assemblies 1016–1020 holding the rod 1002. Once a desired arrangement is obtained, the nuts 1022 may be tightened, thereby securing the clamp assemblies 1016–1020. Thus, with a system in accordance with the present invention, each individual clamp assembly is uniaxial, i.e., may only be pivoted about a single axis. By setting the axes of the anchor screws substantially transverse relative to one another, substantially flexibility may be obtained without substantially compromising vertebra position. Because of the uniaxial nature of the clamp assemblies, however, the system may be less likely to become misaligned when the patient resumes normal activity than a polyaxial system.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the spirit and scope of the appended claims.

What is claimed is:

1. An anchor screw assembly for a spinal fixation system, comprising:
    a screw having a first threaded portion terminating in a tip, and a second head portion opposite the tip comprising a shoulder;
    a swing bolt pivotally coupled to the second portion of the screw;
    a clamp assembly comprising a first passage therethrough for receiving the swing bolt therethrough, the clamp assembly comprising a second passage extending substantially transversely to the first axis when received on the hub; and
    a fastener attachable to the swing bolt for securing the clamp assembly on the swing bolt, the clamp assembly substantially engaging the shoulder when the clamp assembly is secured on the swing bolt, thereby preventing the swing bolt from pivoting with respect to the screw.

2. The anchor screw assembly of claim 1, wherein the swing bolt comprises a noncircular region, and wherein the first passage through the clamp assembly has a noncircular cross-section similar to the noncircular region.

3. The anchor screw assembly of claim 2, wherein the noncircular region has a noncircular cross-section configured to be received in the first passage to prevent rotation of the clamp assembly about the first axis with respect to the swing.

4. The anchor screw assembly of claim 2, wherein the noncircular cross-section comprises a generally circular cross-section having one or more flattened regions.

5. The anchor screw assembly of claim 2, wherein the first passage comprises an elongate slot, having a length substantially longer than the noncircular region of the swing bolt, whereby the swing bolt may be disposed in a plurality of locations along the slot while preventing rotation of the clamp assembly with respect to the swing bolt.

6. The anchor screw assembly of claim 1, wherein the swing bolt comprises a threaded region opposite the screw, and wherein the fastener comprises a nut threadable onto the threaded region.

7. The anchor screw assembly of claim 6, wherein the swing bolt comprises a smooth walled region for slidably receiving the clamp assembly thereon, the smooth walled region being located between the threaded region and the screw.

8. The anchor screw assembly of claim 1, wherein the clamp assembly comprising first and second clamp portions, each clamp portion having a first passage therethrough for receiving the hub of the swing bolt therethrough, the first and second clamp portions having cooperating grooves therein, the cooperating grooves together defining the second passage when the first and second clamp portions are received on the hub.

9. The anchor screw assembly of claim 8, wherein the shoulder is radiused, and wherein the first clamp portion comprises a recess adjacent a lower surface of the first clamp portion that intersects the first passage, the recess having a radiused shape for pivotally receiving the shoulder therein before the clamp assembly is fully secured on the swing bolt.

10. The anchor screw assembly of claim 9, wherein the first passage comprises an elongate slot, having a length substantially longer than the noncircular region of the swing bolt, whereby the swing bolt may be disposed in a plurality of locations along the slot while preventing rotation of the clamp assembly with respect to the swing bolt, and wherein the first clamp portion comprises a plurality of recesses adjacent the lower surface of the first clamp portion that intersects the first passage for pivotally receiving the shoulder in one of a plurality of locations before the clamp assembly is fully secured on the swing bolt.

11. An anchor screw assembly for a spinal fixation system, comprising:
    a screw having a first threaded portion, and a second portion;
    a swing bolt pivotally coupled to the second portion of the screw, the swing bolt defining a first axis and comprising a noncircular region extending along the first axis, the noncircular region having a noncircular cross-section;
    a clamp assembly comprising first and second clamp portions, each clamp portion having a noncircular first passage therethrough for receiving the noncircular region of the swing bolt therethrough, the first and second clamp portions having cooperating grooves therein, the cooperating grooves together defining a second passage extending substantially transversely to the first axis when the first and second clamp portions are received on the swing bolt; and
    a fastener for securing the clamp assembly on the swing bolt.

12. The anchor screw assembly of claim 11, wherein the second portion of the screw comprises a shoulder, and wherein the clamp assembly substantially engages the shoulder when the clamp assembly is fully secured on the swing bolt, thereby preventing the swing bolt from pivoting with respect to the screw.

13. The anchor screw assembly of claim 12, wherein the shoulder is radiused, and wherein the first clamp portion comprises a recess adjacent a lower surface of the first clamp portion that intersects the first passage, the recess having a radiused shape for pivotally receiving the shoulder therein before the clamp assembly is fully secured on the swing bolt.

14. The anchor screw assembly of claim 13, wherein the first passage comprises an elongate slot, having a length substantially longer than the noncircular region of the swing bolt, whereby the swing bolt may be disposed in a plurality of locations along the slot while preventing rotation of the clamp assembly with respect to the swing bolt, and wherein the first clamp portion comprises a plurality of recesses adjacent the lower surface of the first clamp portion that intersects the first passage for pivotally receiving the shoulder in one of a plurality of locations before the clamp assembly is fully secured on the swing bolt.

15. The anchor screw assembly of claim 11, wherein the noncircular cross-section of the noncircular region and the first passage prevents rotation of the clamp assembly with respect to the swing bolt about the first axis when the noncircular region of the swing bolt is received in the first passages.

16. The anchor screw assembly of claim 11, wherein the noncircular cross-section of the noncircular region comprises a generally circular shape having one or more flattened regions.

17. The anchor screw assembly of claim 11, wherein the noncircular region comprises a generally cylindrical shape having at least one flattened region extending along the noncircular region.

18. The anchor screw assembly of claim 11, wherein the swing bolt further comprises a threaded region opposite the screw, and wherein the fastener comprises a nut threadable onto the threaded region of the swing bolt.

19. The anchor screw assembly of claim 18, wherein the noncircular region comprises a smooth walled region for slidably receiving the clamp assembly thereon, the smooth walled region being located between the threaded region and the screw, the threaded region having a cross-section smaller than the noncircular region.

20. The anchor screw assembly of claim 11, wherein the clamp assembly defines a third axis extending along a centerline of the clamp assembly between the first passage towards the second passage, and wherein the third axis is substantially perpendicular to the second axis.

21. The anchor screw assembly of claim 11, wherein the clamp assembly defines a third axis extending along a centerline of the clamp assembly between the first passage towards the second passage, and wherein the third axis defines an acute angle with the second axis.

22. A spinal fixation system, comprising:
a first anchor screw assembly comprising a first screw having a threaded portion, a swing bolt pivotally coupled to the screw and comprising a noncircular region extending along a first longitudinal axis of the swing bolt, a first clamp assembly comprising a first passage for receiving the first swing bolt therethrough, the noncircular region and the first passage having similar cross-sections, and a fastener for securing the first clamp assembly on the swing bolt, the first clamp assembly comprising a second passage therethrough along a second axis substantially transverse to the first axis;
a second anchor screw assembly comprising a second screw having a threaded portion and a hub, a second clamp assembly receivable on the hub, and defining a third passage therethrough along a third axis substantially transverse to the first axis; and
an elongate member receivable through the second and third passages.

23. The spinal fixation system of claim 22, wherein the hub is fixed to the second screw.

24. The spinal fixation system of claim 22, wherein the hub is pivotally attached to the second screw.

25. The spinal fixation system of claim 24, wherein the hub is pivotable about an axis that is substantially perpendicular to an axis about which the swing bolt is pivotable when the elongate member is received through the second and third passages.

26. The spinal fixation system of claim 22, wherein the noncircular cross-section of the noncircular region and the first passage prevents rotation of the first clamp assembly about the first axis with respect to the swing bolt when the noncircular region is received through the first clamp assembly.

27. The spinal fixation system of claim 22, wherein the swing bolt comprises a threaded region opposite the first screw, and wherein the fastener comprises a nut threadable onto the threaded region of the swing bolt.

28. The spinal fixation system of claim 27, wherein the noncircular region comprises a smooth walled region for slidably receiving the first clamp assembly thereon, the smooth walled region being located between the threaded region and the first screw.

29. The spinal fixation system of claim 22, wherein the first clamp assembly comprises first and second clamp portions, each clamp portion having a first passage therethrough for receiving the first hub therethrough, the first and second clamp portions having cooperating grooves therein, the cooperating grooves together defining the second passage when the first and second clamp portions are received on the swing bolt.

30. The spinal fixation system of claim 22, wherein the second and third passages have noncircular cross-sections, and wherein the elongate member has a similar noncircular cross-section.

31. The spinal fixation system of claim 22, wherein the first screw comprises a shoulder adjacent the swing bolt, and wherein the first clamp assembly substantially engages the shoulder when the first clamp assembly is secured on the swing bolt, thereby preventing the swing bolt from pivoting with respect to the first screw.

32. An anchor screw assembly for a spinal fixation system, comprising:
an anchor screw having a first threaded portion, and a second head portion defining a longitudinal axis, the head portion comprising a noncircular region extending along the longitudinal axis, the noncircular region having a noncircular cross-section, the threaded portion comprising a pull-out portion adjacent the head portion;
a clamp assembly comprising upper and lower clamp portions, each clamp portion having a noncircular first passage therethrough for receiving the noncircular region of the head portion therethrough to prevent substantial rotation of the clamp assembly with respect to the head portion about the longitudinal axis, the upper and lower clamp portions having cooperating grooves therein, the cooperating grooves together defining a second passage extending along a second axis substantially transversely to the first axis when the upper and lower clamp portions are received on the swing bolt, the upper clamp portion comprising a lower surface including one of the cooperating grooves therein, and an upper surface including a raised shoulder above the one of the cooperating groove and a recessed area adjacent the raised shoulder and above the first passage; and
a nut for securing the clamp assembly on the head portion, the nut being received in the recessed area, thereby minimizing a height profile of the anchor screw assembly.

33. The anchor screw assembly of claim 32, wherein the noncircular cross-section of the noncircular region comprises a generally circular shape having one or more flattened regions.

34. The anchor screw assembly of claim 32, wherein the head portion is pivotally fixed to the threaded portion.

35. The anchor screw assembly of claim 32, wherein the head portion is nonpivotally fixed to the threaded portion.

36. The anchor screw assembly of claim 32, wherein the clamp assembly defines a third axis extending along a centerline of the clamp assembly between the first passage towards the second passage, and wherein the third axis is substantially perpendicular to the second axis.

37. The anchor screw assembly of claim 32, wherein the clamp assembly defines a third axis extending along a centerline of the clamp assembly between the first passage towards the second passage, and wherein the third axis defines an acute angle with the second axis.

38. A method for stabilizing vertebrae relative to one another using a plurality of swing bolt anchor screws, each swing bolt anchor screw comprising a swing bolt pivotally coupled to a threaded portion, the vertebrae being disposed adjacent one another along a central spinal axis, the method comprising:
  screwing a threaded portion of a first swing bolt anchor screw into a first vertebra until a first pivot axis of the first swing bolt anchor screw has a predetermined orientation with respect to the spinal axis;
  screwing a threaded portion of a second swing bolt anchor screw into a second vertebra adjacent the first vertebra until a second pivot axis of the second swing bolt anchor screw is substantially transverse to the first pivot axis;
  adjusting an angle of one or more swing bolts on the first and second swing bolt anchor screws about the first and second pivot axes;
  placing lower clamp portions on the swing bolts of the first and second swing bolt anchor screws;
  placing a rod on the lower clamp portions, the rod extending at least between the first and second anchor screws; and
  securing upper clamp portions on the swing bolts of the first and second swing bolt anchor screws, thereby securing the rod between the upper and lower clamp portions.

39. The method of claim 38, further comprising:
  screwing a threaded portion of a third anchor screw into a third vertebra adjacent the first vertebra;
  placing a lower clamp portion on the third anchor screw;
  placing the rod on the lower clamp portion of the third anchor screw, the rod thereby also extending between the first swing bolt anchor screw and the third anchor screw; and
  securing an upper clamp portion on the third anchor screw, thereby securing the rod between the upper and lower clamp portions on the third anchor screw.

40. The method of claim 39, wherein the third anchor screw comprises a third swing bolt anchor screw, wherein the threaded portion of the third swing bolt anchor screw is screwed into the third vertebra until a third pivot axis of the third swing bolt anchor screw is substantially transverse to the first pivot axis, and wherein the lower and upper clamp portions are placed on a swing bolt of the third swing bolt anchor screw.

41. The method of claim 40, further comprising adjusting an angle of the swing bolt of the third swing bolt anchor screw about the third pivot axis.

42. The method of claim 39, wherein the third anchor screw comprises a nonpivotable anchor screw.

43. The method of claim 38, wherein the threaded portions of the first and second swing bolt anchor screws comprise head portions including shoulders, the swing bolts being pivotally coupled to the head portions, and wherein the upper clamp portions are secured on the swing bolts until the lower clamp portions frictionally engage the shoulders, thereby securing the swing bolts with respect to the threaded portions.

44. The method of claim 38, wherein the swing bolts comprise noncircular regions, and wherein the upper and lower clamp portions comprise noncircular passages for engaging the noncircular regions when received on the swing bolts, thereby preventing the upper and lower clamp portions from rotating with respect to the swing bolts.

45. The method of claim 38, wherein the swing bolts comprise threaded regions, and wherein the upper clamp portions are secured on the swing bolts by threading a fastener onto the threaded regions.

46. The method of claim 38, further comprising bending the rod to a predetermined configuration based upon anatomy encountered before securing the upper clamp portions on the swing bolts.

47. The method of claim 38, wherein the predetermined orientation of the first pivot axis is generally parallel to the spinal axis.

* * * * *